United States Patent [19]

Peterson et al.

[11] Patent Number: 4,480,639

[45] Date of Patent: Nov. 6, 1984

[54] MEDICAL TUBE RETAINING DEVICE

[76] Inventors: Edward D. Peterson, 1036 Glenhill Rd.; A. Dale Godfrey, 4909 Dehesa Rd.; Claire R. Douglas, 1353 Monument Hill Rd., all of El Cajon, Calif. 92020; Carl R. Pennington, 1917 Maplebrook Ct., El Cajon, Calif. 92021

[21] Appl. No.: 423,659

[22] Filed: Sep. 27, 1982

Related U.S. Application Data

[63] Continuation-in-part of Ser. No. 339,975, Jan. 18, 1982, abandoned.

[51] Int. Cl.³ .............................................. A61M 25/02
[52] U.S. Cl. ......................... 128/207.18; 128/DIG. 26; 604/179
[58] Field of Search ...................... 128/207.17, 207.18, 128/133, DIG. 26; 604/179, 174

[56] References Cited

U.S. PATENT DOCUMENTS

| 3,161,199 | 12/1964 | Sands | 128/207.18 X |
| 3,209,755 | 10/1965 | McCarthy et al. | 128/DIG. 26 |
| 3,648,703 | 3/1972 | Manker | 128/207.18 X |
| 4,282,871 | 8/1981 | Chodorow et al. | 128/207.18 |
| 4,351,331 | 9/1982 | Gereg | 128/207.17 |

Primary Examiner—Dalton L. Truluck
Attorney, Agent, or Firm—Brown, Martin & Haller

[57] ABSTRACT

A simple, one piece medical tube retaining device. The device is particularly adapted for retaining a nasal tube in position on the face of the user and including a flexible strap with a first clamp means positioned beneath the nose of the user for clamping the tube and preventing undesired movement of the tube while accommodating required movement, and second clamp means near one end of the strap means to hold said tube in position, the clamp means being constructed to facilitate insertion and removal of the tube.

3 Claims, 9 Drawing Figures

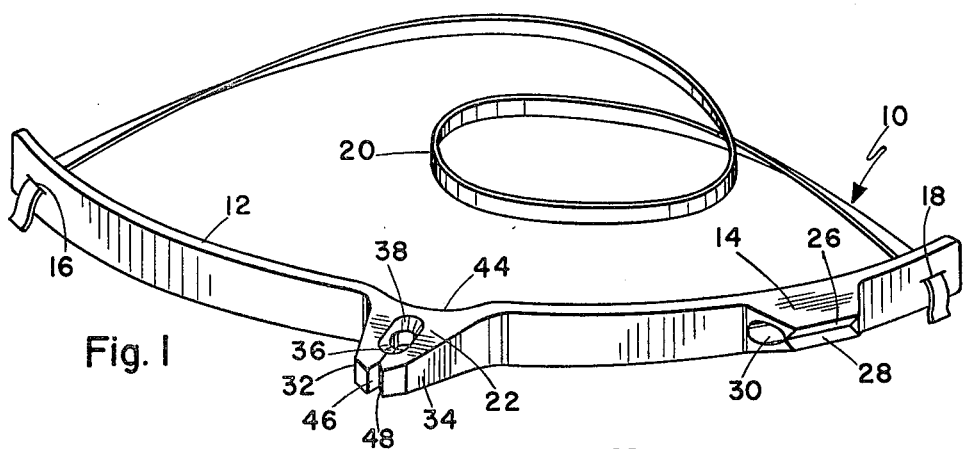
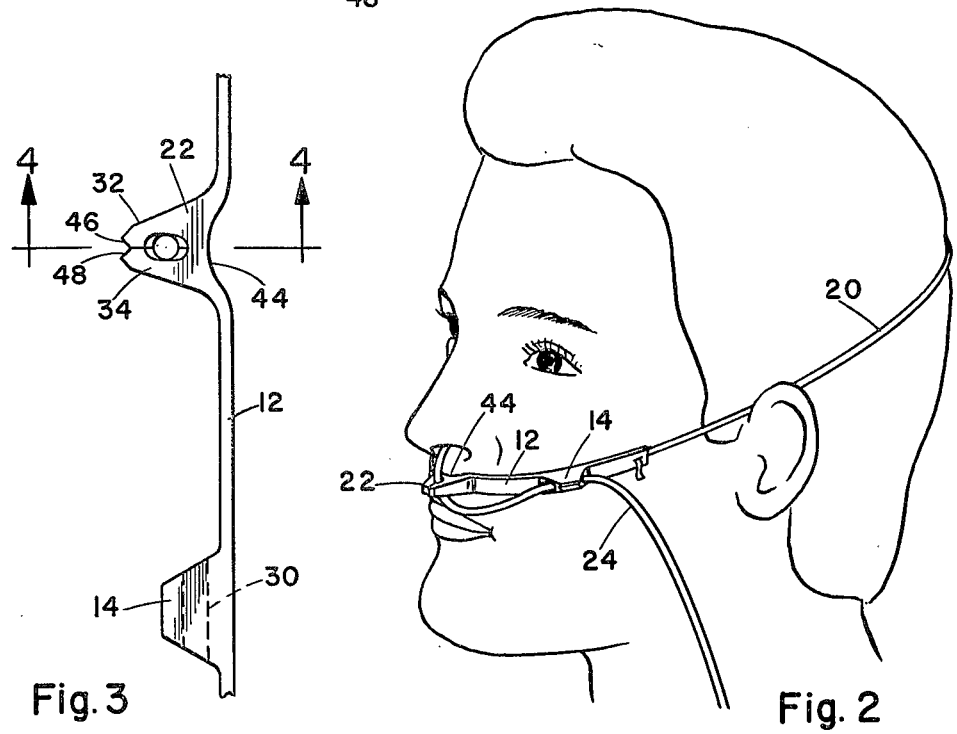
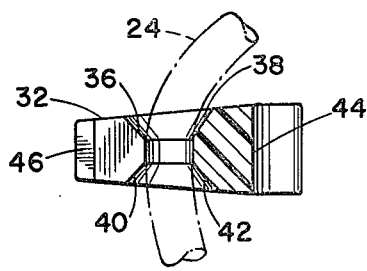
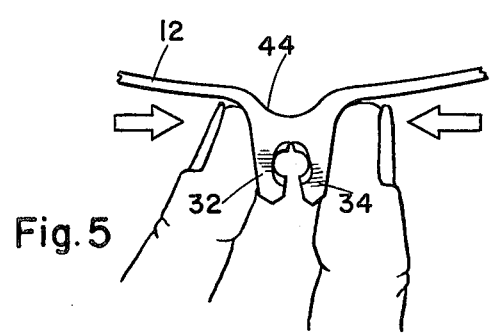

MEDICAL TUBE RETAINING DEVICE

This application is a continuation-in-part of patent application Ser. No. 339,975 filed Jan. 18, 1982 now abandoned.

BACKGROUND OF THE INVENTION

The present invention relates to a medical tube retaining device for retaining in position a medical tube extending from an opening in a patient. It particularly relates to such a device for use with nasal tubes extending from the nose of the patient.

Hospital patients are subjected to great discomfort when they are required to use medical tubes such as gastric tubes which extend through the nose of the patient down into the stomach. Bending and twisting of the tube after it is in position causes severe pain. These tubes are normally taped to the patient's face with adhesive tape in an attempt to hold them firmly in position and reduce the pain to the patient. The adhesive tape constantly pulls on the patient's skin and pulls the tube against mucus membrances of the nose which is uncomfortable even in the best of circumstances. The adhesive tape cannot position the tube from the nose to the medical device, such as a suction apparatus, in a manner which avoids discomfort.

Several attempts have been made to provide a device which would replace the use of adhesive tape in positioning the medical tube along the face of the patient. One such device is shown in U.S. Pat. No. 4,284,076 wherein a short, thick block of material includes spring members to secure the nasal tube in the position. This is the only retaining means and the tube extends straight out of the patient's nostril.

Another device is shown in U.S. Pat. No. 3,161,199 where again the only securing means is located beneath the nose and the tube extends straight out from the nose.

U.S. Pat. No. 3,972,321 shows a short band with a clamp in the center. The clamp is the only securing means and the tube extends straight out from the nose.

U.S. Pat. No. 3,648,703 discloses a tubular member that houses the stomach tube and carries it along the side of the face of the patient. The stomach tube must be inserted through the container tube into the nose of the patient so that the tube is inserted at an angle.

U.S. Pat. No. 2,868,199 discloses a cannula for providing oxygen to the patient. It includes a main tube having small tube extensions that are positioned within the nostrils of the user.

None of these prior art devices provide a simple, inexpensive, easy to use device which minimizes the discomfort to the patient.

It is a primary object of the present invention to provide a new and improved medical tube retaining device that is simple in construction and easy to apply, and that is economical to manufacture.

It is another object of the present invention to provide a new and improved medical tube retaining device, particularly adapted for use with nasal tubes, that is versatile in use and that positions the tube for minimum discomfort to the patient while effectively securing the tube to prevent accidental removal.

It is a further object of the present invention to provide a new and improved medical tube retaining device involving a tube clamp construction that is simple and very easy to use.

SUMMARY OF THE INVENTION

The shortcomings of the prior art are overcome and the above objectives are obtained by an exemplary embodiment of the present invention wherein flexible strap means includes a first clamp means for positioning beneath the nose of the patient and permits the tube to self-adjust while restricting it in directions which may cause discomfort or injury. A second clamp means is positioned near one end of the strap means to provide the primary tube gripping means along the face of the patient. The clamp means are quickly and easily opened and closed to accommodate insertion and removal of the tube.

DESCRIPTION OF THE DRAWINGS

FIG. 1 is a perspective view of a medical tube retaining device embodying the present invention.

FIG. 2 illustrates the device in use.

FIG. 3 is a top plan view of the tube holding elements.

FIG. 4 is an enlarged sectional view taken on line 4—4 of FIG. 3.

FIG. 5 illustrates the technique of squeezing open the central tube holding element.

DETAILED DESCRIPTION OF THE INVENTION

Figure 6:
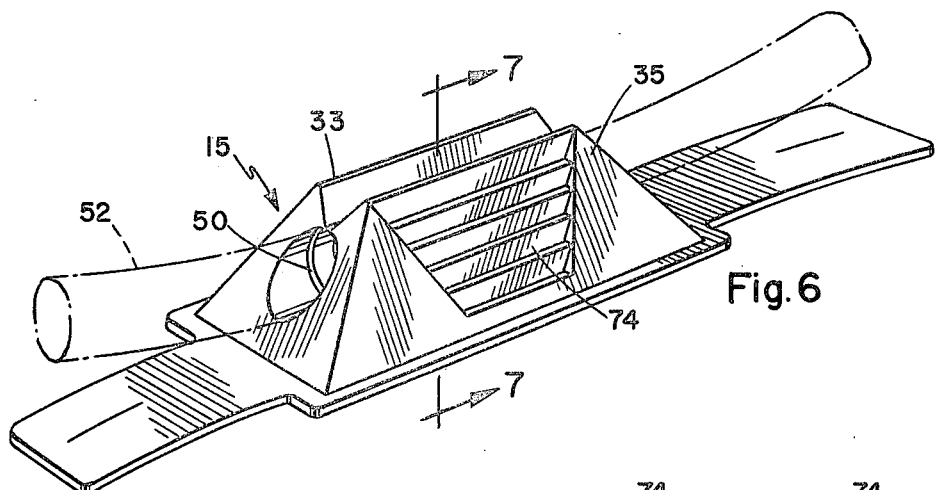
FIG. 6 is a perspective view of a single tube clamp which also can be used as the primary tube clamp with the medical tube retaining device shown in FIGS. 1-5.

Referring to FIGS. 1-5 of the drawings, a medical tube retaining device embodying the present invention is shown at 10. The device includes a strap 12 of flexible material such as polyvinyl plastic for example. The strap includes a primary tube clamp 14 toward one end and fastening slots 16 and 18 adjacent the ends. A fastening band 20 is secured through the slots of strap 12 and may be formed of an elastic material to hold the band in position when it is in use. The band 12 also includes a tube positioning clamp 22 near the center thereof.

The retaining device is a single piece of simple inexpensive construction with a fastening means such as the headband connected to it. The device is shown in use in FIG. 2 of the drawings with the tube positioning clamp 22 located beneath the nose of the user and the primary tube clamp 14 positioned on the cheek of the user. A nasal gastric tube 24 is shown extending into the nose of the user from a hospital device such as a suction device (not shown). The tube is retained in position by the clamps 14 and 22. The fastening band 20 extends around the head of the user to hold the strap 12 in place. The length of the fastening device can be adjusted by simply pulling an end or ends through one way or the other in the slots.

The device is constructed so that the primary clamp can be positioned on either cheek. The patient's head will normally be placed so that the primary clamp and tube are away from the pillow. If he desires to lie on the other side of his face, the strap can be quickly and easily reversed to accommodate this change in position. The primary clamp 14 has tapered tips 26 and 28 which serve as a guide when inserting the tube 24 into the primary tube clamp 14. The tube 24 can be removed from the primary clamp 14 merely by inserting the finger beneath one tip and spreading the clamp to enlarge the opening 30 for releasing the tube.

Positioning of the tube beneath the nose of the user to minimize discomfort to the patient is extremely important. The positioning clamp 22 is simple and effective. It includes a pair of fingers 32 and 34 that are normally closed together as shown in FIGS. 1-3 of the drawings. Each finger includes cut out portions 36, 38, 40 and 42. This configuration permits the tube 24 to adjust forward and rearward as dictated by the comfort of the patient but the tube is restricted against sidewise movement which can be painful or cause injury. A notch 44 at the base of the positioning clamp accommodates the philtrum which is the extending portion of the face beneath the nose and the upper lip of the user. Some people have prominent philtrums and this construction avoids pressing of the device on the philtrum and avoids accumulation of perspiration beneath the nose of the patient normally caused by the use of such devices.

The notch also serves a second important function. When the positioning clamp is gripped at the base with the user's fingers as shown in FIG. 5 of the drawings, the clamp fingers 32 and 34 of the clamp quickly and easily spread open releasing the tube 24. When the clamp fingers 32 and 34 are closed, the spreading force applied at the base of the tube positioning clamp 22 by the fastening band urges the ends of the clamp fingers together. The ends of the clamp fingers are tapered at 46 and 48 to provide a guide when inserting the tube into the tube positioning clamp 22. A person's finger tip can be inserted to aid in spreading the fingers 46 and 48 to a wide open position, although this is not normally required.

The device for the present invention is light and comfortable. It is a one piece pliable plastic construction that accommodates movement with no moving parts. It is easy for the nurse and the patient to understand and use. The device can be easily cleaned and can be manufactured at sufficiently low cost so that it can be considered disposable if desired. The tube positioning clamp 22 adjusts the position of the tube 24 at the point where the tube 24 extends from the nose. The primary clamp 14 directs the tube back to the hookup device (not shown) away from the mouth and the face of the patient. This allows the patient easy access to the mouth area. The strap 12 is flexible and adjusts readily to the contour of the patient's face.

Although the clamping device is primarily intended for use with a nasal gastric tube, it can be used on other parts of the anatomy to hold a tube that is inserted in an opening in the patient's body. For example, the device could be placed around the patient's leg to position the tube as it extends from the body opening to a hookup for purposes such as gravity urinary drainage or to secure an intravenous tube or multiple intravenous tubes.

Figure 7:
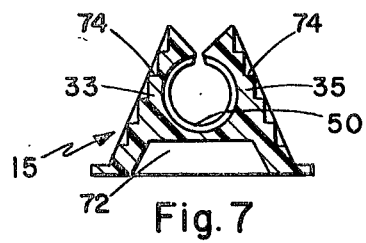
FIG. 7 is a sectional view taken on line 7—7 of FIG. 6.

A second embodiment with a single tube clamp is shown in FIGS. 6 and 7 of the drawings. The clamp 15 includes a hollowed or cut out portion 72 which enables the clamp 15 to be quickly and easily opened and closed. The clamp 15 is opened by squeezing the clamp fingers 33 and 35 together near the center and bottom. The bottom of the clamp 15 is compressed and the clamp fingers 33 and 35 spread apart. The tube 52 is then inserted in or removed from the clamp 15 as desired. The clamp 15 has ridged or stepped portions 74 on the external portion of clamp fingers 33 and 35. This prevents slippage when the clamp fingers are engaged by the fingers of the user. The inside of the clamp 15 includes rifling or lands 50 which aids the tube clamp fingers 33 and 35 in holding the tube 52 in position. This tube clamp 15 can also be used as the primary tube clamp 14 with the construction shown in FIGS. 1-5 of the drawings.

Figure 8:
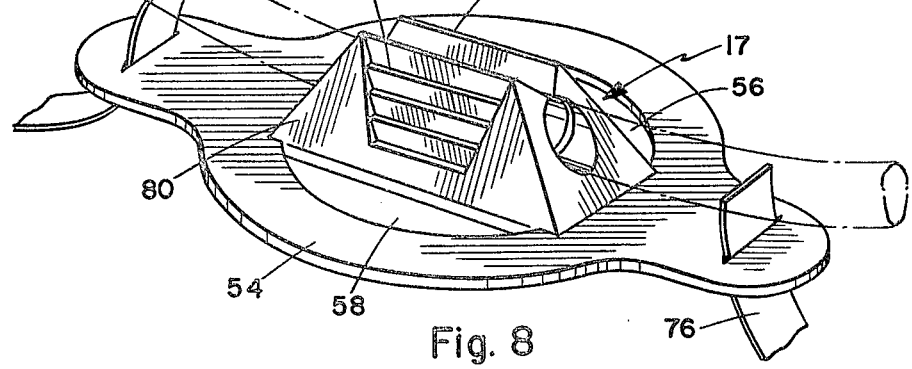
FIG. 8 is a perspective view of a further type of single tube clamp.

The tube clamp shown in FIGS. 6 and 7 of the drawings is useful in other applications as shown for example in FIG. 8 of the drawings. The clamp indicated at 17 is used with a catheter tube 52. The clamp 17 has a hollow back portion the same as shown in FIGS. 6 and 7 of the drawings. The clamp 17 is an integral part of a flexible support pad 54 which has open positions 56 and 58 to permit the clamp 17 to open and close freely. An elastic band 76 is adapted to extend around the arm or leg of a patient. Squeezing of the clamp fingers 78 and 80 quickly and easily spreads them with freedom due to the openings 56 and 58.

Figure 9:
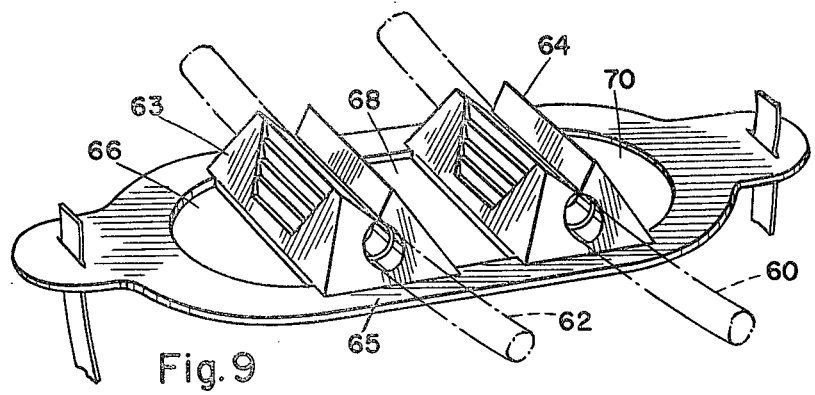
FIG. 9 is perspective view of a double tube clamp.

FIG. 9 discloses a further embodiment wherein multiple tubes 60 and 62 are supported in clamps 63 and 64 on the support pad 65. Openings 66, 68 and 70 in support pad 65 permit the tube clamps 63 and 64 to be easily opened and closed.

Having thus described our invention, we claim:

1. A one piece device for positioning and retaining a nasal tube on the face of a patient, comprising:
    flexible straps means for positioning beneath the nose and extending to a point on each side of the face along the check of the user;
    first tube clamp means on said strap means for positioning beneath the nose of the user and holding a tube extending from the nose of the user, said first tube clamp means including a block having a cutout portion for placing over the philtrum of the user, and a pair of outwardly extending fingers surrounding a tube receiving opening, the sides of said cutout portion being squeezable to open said fingers, and tension on the ends of said strap means tending to close said fingers;
    the said tube receiving opening in said first tube clamp means is formed to accommodate tilting movement of said tube forward and back and to restrict sidewise movement of said tube;
    second tube clamp means on said strap means near one end of said strap means for gripping said tube along said strap means, said second tube clamp means readily accommodating insertion and removal of said tube;
    each end of said strap means being connectable to a holding means that positions around the head of the user to hold said strap means in position.

2. A one piece device for positioning and retaining a medical tube, comprising:
    flexible strap means for positioning on the user;
    first tube clamp means on the said strap means near the center thereof for holding a tube extending from an opening in the user, wherein said first tube clamp means includes a block having a cutout portion and a pair of outwardly extending fingers surrounding a tube receiving opening, the sides of said cutout portion being squeezable to open said fingers, and tension on the ends of said strap means tending to close said fingers; and a second tube clamp means on said strap means near one end thereof for gripping said tube along said strap means;

each end of said strap means being connectable to a holding means for holding said strap means to the user.

3. A one piece device for positioning and retaining a nasal tube on a patient comprising:

flexible strap means for positioning beneath the nose and extending to a point on each side of the face along the cheek of the user;

first tube clamp means on said strap means for positioning beneath the nose of the user and holding a tube extending from the nose of the user, wherein said first tube clamp means includes a block having a cutout portion for placing over the philtrum of the user and a pair of outwardly extending fingers surrounding a tube receiving opening, the sides of said cutout portion being squeezable to open said fingers, and tension on the end of said strap means tending to close said fingers; and a second tube clamp means on said strap means near one end of said strap means for gripping said tube along said strap means;

each end of said strap means being connectable to a holding means that positions around the head of the user to hold said strap means in position, and each said clamp means being constructed to permit the device to clamp said tube along either side of the face of the user.

* * * * *